US006995000B2

(12) United States Patent
Bathe et al.

(10) Patent No.: US 6,995,000 B2
(45) Date of Patent: Feb. 7, 2006

(54) NUCLEOTIDE SEQUENCES CODING FOR THE SIGM GENE

(75) Inventors: Brigitte Bathe, Salzkotten (DE);
Christine Bastuck, Bielefeld (DE);
Mike Farwick, Bielefeld (DE);
Thomas Hermann, Bielefeld (DE);
Walter Pfefferle, Halle (DE)

(73) Assignee: Degussa, Düsseldorf (DE)

( * ) Notice: Subject to any disclaimer, the term of this patent is extended or adjusted under 35 U.S.C. 154(b) by 179 days.

(21) Appl. No.: 09/942,935

(22) Filed: Aug. 31, 2001

(65) Prior Publication Data

US 2002/0106755 A1  Aug. 8, 2002

(30) Foreign Application Priority Data

Sep. 2, 2000 (DE) ................. 100 43 337
Jul. 28, 2001 (DE) ................. 101 36 984

(51) Int. Cl.
*C12P 13/04* (2006.01)

(52) U.S. Cl. .................. 435/106; 435/115; 435/320.1; 435/252.32; 435/252.33; 536/23.1; 536/23.2; 536/24.3; 536/24.33

(58) Field of Classification Search ............... 536/23.1, 536/23.5, 23.7, 24.3, 24.33, 23.2; 435/320.1, 435/252.3, 252.32, 254.11, 419, 325, 252.33, 435/252.1, 106, 115
See application file for complete search history.

(56) References Cited

U.S. PATENT DOCUMENTS

2002/0197605 A1 * 12/2002 Nakagawa et al. ............ 435/6

FOREIGN PATENT DOCUMENTS

EP         1108790 A2 *  6/2001
WO    WO 200100843 A2 *  1/2001

OTHER PUBLICATIONS

Amador et al. Structure and organization of the rrnD operon of 'Brevibacterium lactofermentum': analysis of the 16S rRNA gene. Microbiology (1999) 145: 915-924.*
Zhao et al. GenBank Accession No. AZ241095. RPCl-23-35N21.TV RPCl-23 Mus musculus genomic clone RCPl-23-35N21, genomic survey sequence. Jun. 15, 2000.*
Oguiza et al., "Multiple sigma factor genes in Brevibacterium lactofermentum: characterization of sigA and sigB", Journal of Bacteriology, vol. 178, No. 2, Jan. 1996, pp. 550-553.
Marjorie L. Beggs, et al., "Isolation and sequence of a *Mycobacterium tuberculosis* sigma factor", Gene 174 (1996) pp. 285-287.

* cited by examiner

*Primary Examiner*—Kathleen Kerr
(74) *Attorney, Agent, or Firm*—Smith, Gambrell & Russell LLP

(57) ABSTRACT

The invention relates to an isolated polynucleotide from *Corynebacterium glutamicum* having a polynucleotide sequence which encodes the sigma factor M (sigM) gene, and a host-vector system having a coryneform host bacterium in which the sigM gene is present in enhanced form and a vector which carries at least the sigM gene according to SEQ ID No 1, and the use of polynucleotides which comprise the sequences according to the invention as hybridization probes.

17 Claims, 2 Drawing Sheets

Figure 2: Map of plasmid pEC-XK99EsigMa1ex
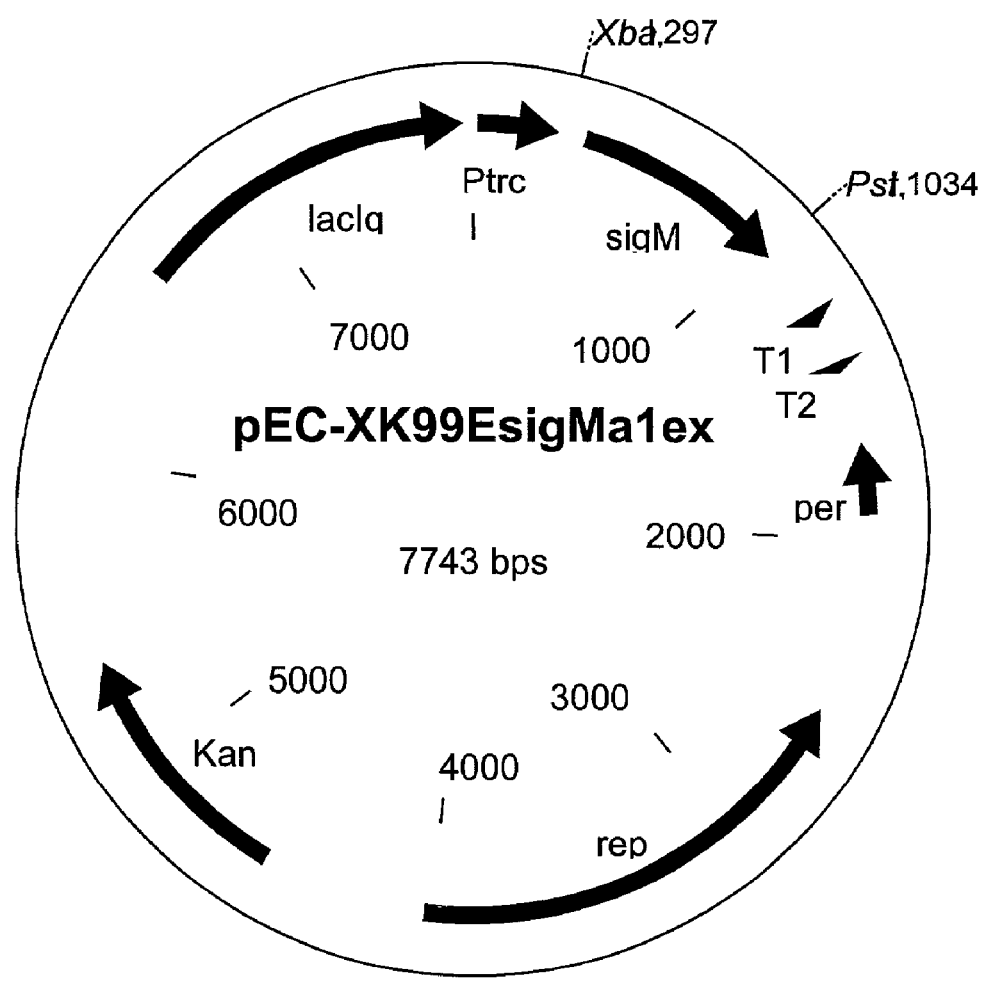

NUCLEOTIDE SEQUENCES CODING FOR THE SIGM GENE

BACKGROUND OF THE INVENTION

The invention provides nucleotide sequences from coryneform bacteria coding for the sigM gene, and a process for the production of amino acids by fermentation using bacteria in which the endogenous sigM gene is enhanced. All references cited herein are expressly incorporated by reference. Incorporation by reference is also designated by the term "I.B.R." following any citation.

L-amino acids, especially lysine, are used in human medicine and in the pharmaceuticals industry, in the foodstuffs industry and, very especially, in the feeding of animals.

It is known that amino acids are produced by fermentation of strains of coryneform bacteria, especially *Corynebacterium glutamicum*. Because of their great importance, attempts are continuously being made to improve the production processes. Improvements to the processes may concern measures relating to the fermentation, such as, for example, stirring and oxygen supply, or the composition of the nutrient media, such as, for example, the sugar concentration during the fermentation, or working up to the product form by, for example, ion-exchange chromatography, or the intrinsic performance properties of the microorganism itself.

In order to improve the performance properties of such microorganisms, methods of mutagenesis, selection and mutant selection are employed. Such methods yield strains which are resistant to antimetabolites or are auxotrophic for metabolites that are important in terms of regulation, and which produce amino acids.

For a number of years, methods of recombinant DNA technology have also been used for improving the strain of L-amino acid-producing strains of *Corynebacterium*, by amplifying individual amino acid biosynthesis genes and studying the effect on amino acid production.

The invention provides novel measures for the improved production of amino acids by fermentation.

BRIEF SUMMARY OF THE INVENTION

Where L-amino acids or amino acids are mentioned hereinbelow, they are to be understood as meaning one or more amino acids, including their salts, selected from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. Lysine is particularly preferred.

Where L-lysine or lysine are mentioned hereinbelow, they are to be understood as meaning not only the bases but also the salts such as, for example, lysine monohydrochloride or lysine sulfate.

The invention provides an isolated polynucleotide from coryneform bacteria, containing a polynucleotide sequence coding for the sigM gene, selected from the group
a) polynucleotide that is at least 70% identical with a polynucleotide that codes for a polypeptide containing the amino acid sequence of SEQ ID No. 2,
b) polynucleotide that codes for a polypeptide containing an amino acid sequence that is at least 70% identical with the amino acid sequence of SEQ ID No. 2,
c) polynucleotide that is complementary to the polynucleotides of a) or b), and
d) polynucleotide containing at least 15 consecutive nucleotides of the polynucleotide sequence of a), b) or c), the polypeptide preferably exhibiting the activity of sigma factor M.

The invention also provides the above-mentioned polynucleotide, it preferably being a replicable DNA containing:
(i) the nucleotide sequence shown in SEQ ID No. 1, or
(ii) at least one sequence that corresponds to sequence (i) within the region of the degeneracy of the genetic code, or
(iii) at least one sequence that hybridizes with the sequence that is complementary to sequence (i) or (ii), and optionally
(iv) sense mutations in (i) that are neutral in terms of function.

The invention also provides
a replicable polynucleotide, especially DNA, containing the nucleotide sequence as shown in SEQ ID No. 1;
a polynucleotide that codes for a polypeptide containing the amino acid sequence as shown in SEQ ID No. 2;
a vector containing the polynucleotide according to the invention, especially a shuttle vector or plasmid vector, and
coryneform bacteria which contain the vector or in which the endogenous sigM gene has been enhanced.

The invention also provides polynucleotides consisting essentially of a polynucleotide sequence, which are obtainable by screening, by means of hybridization, a corresponding gene library of a coryneform bacteria that contains the complete gene or parts thereof, using a probe containing the sequence of the polynucleotide of the invention according to SEQ ID No. 1 or a fragment thereof, and isolating the mentioned polynucleotide sequence.

BRIEF DESCRIPTION OF THE FIGURES

FIG. 2: Map of plasmid pEC-XK99EsigMa1ex
The abbreviations and names used have the following meanings:

Figure 1:
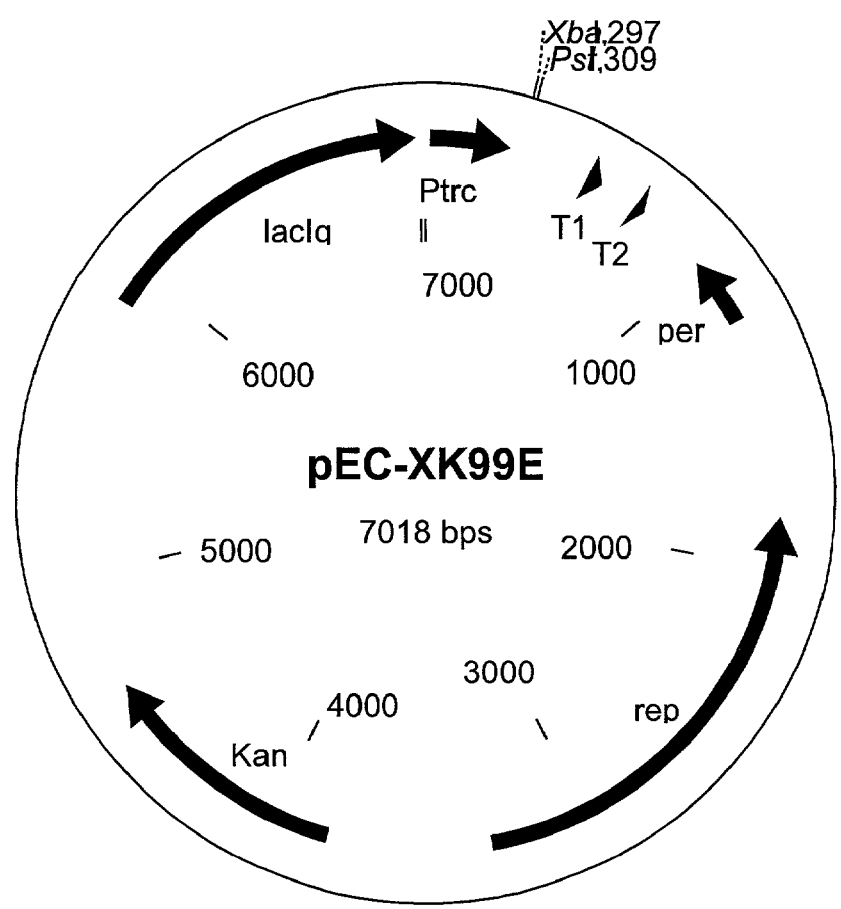
FIG. 1: Map of plasmid pEC-XK99E

| | |
|---|---|
| Kan: | Kanamycin resistance gene aph(3')-IIa from *Escherichia coli* |
| HindIII | Cleavage site of the restriction enzyme HindIII |
| XbaI | Cleavage site of the restriction enzyme XbaI |
| PstI | Cleavage site of the restriction enzyme PstI |
| Ptrc | Trc promoter |
| T1 | Termination region T1 |
| T2 | Termination region T2 |
| Per | Replication effector per |
| Rep | Replication region rep of plasmid pGA1 |
| LacIq | LacIq repressor of the lac operon of *Escherichia coli* |
| SigM | Cloned sigM gene |

DETAILED DESCRIPTION OF THE INVENTION

Polynucleotides that contain the sequences of the invention are suitable as hybridization probes for RNA, cDNA and DNA, in order to isolate in their complete length nucleic acids or polynucleotides or genes that code for sigma factor M, or in order to isolate nucleic acids or polynucleotides or genes that are very similar to the sequence of the sigM gene.

They are also suitable for incorporation into so-called arrays or micro arrays or DNA chips in order to detect and determine the corresponding polynucleotides.

Polynucleotides that contain the sequences of the invention are also suitable as primers, with the aid of which it is possible, by means of the polymerase chain reaction (PCR), to produce DNA of genes that code for sigma factor M.

Such oligonucleotides acting as probes or primers contain at least 25, 26, 27, 28, 29 or 30, preferably at least 20, 21, 22, 23 or 24, most particularly preferably at least 15, 16, 17, 18 or 19, consecutive nucleotides. Also suitable are oligonucleotides having a length of at least 31, 32, 33, 34, 35, 36, 37, 38, 39 or 40 or at least 41, 42, 43, 44, 45, 46, 47, 48, 49 or 50 nucleotides. Oligonucleotides having a length of at least 100, 150, 200, 250 or 300 nucleotides may also be suitable.

"Isolated" means removed from its natural environment.

"Polynucleotide" generally refers to polyribonucleotides and polydeoxyribonucleotides, it being possible for the RNA or DNA to be unmodified or modified.

The polynucleotides of the invention include a polynucleotide according to SEQ ID No. 1 or a fragment prepared therefrom, and also polynucleotides that are at least especially from 70% to 80%, preferably at least from 81% to 85%, particularly preferably at least from 86% to 90%, and most particularly preferably at least 91%, 93%, 95%, 97% or 99% identical with the polynucleotide according to SEQ ID No. 1, or with a fragment prepared therefrom.

"Polypeptides" are to be understood as being peptides or proteins that contain two or more amino acids bonded via peptide bonds.

The polypeptides of the invention include a polypeptide according to SEQ ID No. 2, especially those having the biological activity of sigma factor M, and also those that are at least from 70% to 80%, preferably at least from 81% to 85%, particularly preferably at least from 86% to 90%, and most particularly preferably at least 91%, 93%, 95%, 97% or 99% identical with the polypeptide according to SEQ ID No. 2 and exhibit the mentioned activity.

The invention also provides a process for the production, by fermentation, of amino acids selected from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine, using coryneform bacteria which, in particular, already produce amino acids and in which the nucleotide sequences coding for the sigM gene are enhanced, especially overexpressed.

The term "enhancement" in this connection describes an increase in the intracellular activity of one or more enzymes (proteins) in a microorganism that are coded for by the corresponding DNA, by, for example, increasing the number of copies of the gene or genes, using a strong promoter or using a gene or allele that codes for a corresponding enzyme (protein) having a high level of activity, and optionally by combining those measures.

By the measures of enhancement, especially overexpression, the activity or concentration of the corresponding protein is generally increased by at least 10%, 25%, 50%, 75%, 100%, 150%, 200%, 300%, 400% or 500%, at most up to 1000% or 2000%, based on that of the wild-type protein or the activity or concentration of the protein in the starting microorganism.

The microorganisms provided by the present invention are able to produce L-amino acids from glucose, saccharose, lactose, fructose, maltose, molasses, starch, cellulose or from glycerol and ethanol. They may be representatives of coryneform bacteria, especially of the genus *Corynebacterium*. In the case of the genus *Corynebacterium*, special mention may be made of the species *Corynebacterium glutamicum*, which is known to those skilled in the art for its ability to produce L-amino acids.

Suitable strains of the genus *Corynebacterium*, especially of the species *Corynebacterium glutamicum* (*C. glutamicum*), are especially the known wild-type strains
*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 and L-amino acid-producing mutants or strains prepared therefrom.

The new sigM gene of *C. glutamicum* coding for the enzyme sigma factor M has been isolated.

In order to isolate the sigM gene or other genes from *C. glutamicum*, a gene library of that microorganism in *Escherichia coli* (*E. coli*) is first prepared. The preparation of gene libraries is described in generally known textbooks and handbooks. There may be mentioned as an example the textbook of Winnacker: Gene und Klone, Eine Einführung in die Gentechnologie (Verlag Chemie, Weinheim, Germany, 1990) I.B.R., or the handbook of Sambrook et al.: Molecular Cloning, A Laboratory Manual (Cold Spring Harbor Laboratory Press, 1989) I.B.R. A very well known gene library is that of the *E. coli* K-12 strain W3110, which has been prepared by Kohara et al. (Cell 50, 495–508 (1987)) I.B.R. in λ-vectors. Bathe et al. (Molecular and General Genetics, 252:255–265, 1996) I.B.R. describe a gene library of *C. glutamicum* ATCC13032, which has been prepared with the aid of the cosmid vector SuperCos I (Wahl et al., 1987, Proceedings of the National Academy of Sciences USA, 84:2160–2164 I.B.R.) in the *E. coli* K-12 strain NM554 (Raleigh et al., 1988, Nucleic Acids Research 16:1563–1575 I.B.R.).

Börmann et al. (Molecular Microbiology 6(3), 317–326) (1992)) I.B.R. in turn describe a gene library of *C. glutamicum* ATCC13032 using the cosmid pHC79 (Hohn and Collins, Gene 11, 291–298 (1980) I.B.R.).

For the preparation of a gene library of *C. glutamicum* in *E. coli* it is also possible to use plasmids such as pBR322 (Bolivar, Life Sciences, 25, 807–818 (1979) I.B.R.) or pUC9 (Vieira et al., 1982, Gene, 19:259–268 I.B.R.). Suitable hosts are especially those *E. coli* strains that are restriction—and recombination-defective. An example thereof is the strain DH5αmcr, which has been described by Grant et al. (Proceedings of the National Academy of Sciences USA, 87 (1990) 4645–4649) I.B.R. The long DNA fragments cloned with the aid of cosmids can then in turn be subcloned into customary vectors suitable for sequencing and then sequenced, as is described, for example, in Sanger et al. (Proceedings of the National Academy of Sciences of the United States of America, 74:5463–5467, 1977) I.B.R.

The resulting DNA sequences can then be studied using known algorithms or sequence-analysis programs, such as, for example, that of Staden (Nucleic Acids Research 14, 217–232 (1986)) I.B.R., that of Marck (Nucleic Acids Research 16, 1829–1836 (1988)) I.B.R. or the GCG program of Butler (Methods of Biochemical Analysis 39, 74–97 (1998)) I.B.R.

The novel DNA sequence of *C. glutamicum* coding for the gene sigM has been obtained, which sequence, as SEQ ID No. 1, forms part of the present invention. Furthermore, the amino acid sequence of the corresponding protein has been derived from the present DNA sequence using the methods described above. The resulting amino acid sequence of the sigM gene product is shown in SEQ ID No. 2. It is known that enzymes of the host are able to cleave the N-terminal amino acid methionine or formylmethionine of the protein that is formed.

Coding DNA sequences that result from SEQ ID No. 1 by the degeneracy of the genetic code also form part of the invention. Likewise, DNA sequences that hybridize with SEQ ID No. 1 or parts of SEQ ID No. 1 form part of the invention. Furthermore, to those skilled in the art, conservative amino acid substitutions, such as, for example, the substitution of glycine with alanine or of aspartic acid with glutamic acid, in proteins are known as sense mutations, which do not lead to any fundamental change in the activity of the protein, that is to say are neutral in terms of function. Such mutations are also called neutral substitutions inter alia. It is also known that changes at the N- and/or C-terminus of a protein do not substantially impair its function or may even stabilize it. The person skilled in the art will find relevant information inter alia in Ben-Bassat et al. (Journal of Bacteriology 169:751–757 (1987)) I.B.R., in O'Regan et al. (Gene 77:237–251 (1989)) I.B.R., in Sahin-Toth et al. (Protein Sciences 3:240–247 (1994)) I.B.R., in Hochuli et al. (Bio/Technology 6:1321–1325 (1988)) I.B.R. and in known textbooks of genetics and molecular biology. Amino acid sequences that result in a corresponding manner from SEQ ID No. 2 likewise form part of the invention.

Similarly, DNA sequences that hybridize with SEQ ID No. 1 or parts of SEQ ID No. 1 form part of the invention. Finally, DNA sequences that are produced by the polymerase chain reaction (PCR) using primers that result from SEQ ID No. 1 form part of the invention. Such oligonucleotides typically have a length of at least 15 nucleotides.

The person skilled in the art will find instructions on the identification of DNA sequences by means of hybridization inter alia in the handbook "The DIG System Users Guide for Filter Hybridization" from Boehringer Mannheim GmbH (Mannheim, Germany, 1993) I.B.R. and in Liebl et al. (International Journal of Systematic Bacteriology (1991) 41: 255–260) I.B.R. The hybridization takes place under stringent conditions, that is to say there are formed only hybrids in which the probe and the target sequence, i.e. the polynucleotides treated with the probe, are at least 70% identical. It is known that the stringency of the hybridization, including the washing steps, is influenced or determined by varying the buffer composition, the temperature and the salt concentration. The hybridization reaction is preferably carried out with relatively low stringency as compared with the washing steps (Hybaid Hybridisation Guide, Hybaid Limited, Teddington, UK, 1996 I.B.R.).

There may be used for the hybridization reaction, for example, a 5× SSC buffer at a temperature of approximately from 50 to 68° C. In that case, probes may also hybridize with polynucleotides that are less than 70% identical with the sequence of the probe. Such hybrids are less stable and are removed by washing under stringent conditions. That may be achieved, for example, by lowering the salt concentration to 2× SSC and optionally subsequently to 0.5× SSC (The DIG System User's Guide for Filter Hybridisation, Boehringer Mannheim, Mannheim, Germany, 1995 I.B.R.), a temperature of approximately from 50 to 68° C. being set.

It is optionally possible to lower the salt concentration down to 0.1× SSC. By raising the hybridization temperature stepwise from 50 to 68° C. in steps of approximately from 1 to 2° C., it is possible to isolate polynucleotide fragments that are, for example, at least 70% or at least 80% or at least from 90% to 95% identical with the sequence of the probe used. Further instructions for hybridization are commercially available in the form of so-called kits (e.g. DIG Easy Hyb from Roche Diagnostics GmbH, Mannheim, Germany, Catalog No. 1603558).

The person skilled in the art will find instructions on the amplification of DNA sequences with the aid of the polymerase chain reaction (PCR) inter alia in the handbook of Gait: Oligonucleotide Synthesis: A Practical Approach (IRL Press, Oxford, UK, 1984) I.B.R. and in Newton and Graham: PCR (Spektrum Akademischer Verlag, Heidelberg, Germany, 1994) I.B.R.

It has been found that coryneform bacteria produce amino acids in an improved manner after overexpression of the sigM gene.

In order to achieve overexpression, the number of copies of the corresponding genes can be increased, or the promoter and regulation region or the ribosome binding site, which is located upstream of the structural gene, can be mutated. Expression cassettes inserted upstream of the structural gene have a similar effect. By means of inducible promoters it is additionally possible to increase the expression in the course of the production of amino acids by fermentation. Expression is also improved by measures to prolong the life of the m-RNA. Furthermore, the enzyme activity is also enhanced by preventing degradation of the enzyme protein. The genes or gene constructs may either be present in plasmids with different numbers of copies or be integrated and amplified in the chromosome. Alternatively, overexpression of the genes in question may also be achieved by changing the composition of the medium and the manner in which culturing is carried out.

The person skilled in the art will find instructions thereon inter alia in Martin et al. (Bio/Technology 5, 137–146 (1987)) I.B.R., in Guerrero et al. (Gene 138, 35–41 (1994)) I.B.R., Tsuchiya and Morinaga (Bio/Technology 6, 428–430 (1988)) I.B.R., in Eikmanns et al. (Gene 102, 93–98 (1991)) I.B.R., in EP 0 472 869 I.B.R., in U.S. Pat. No. 4,601,893 I.B.R., in Schwarzer and Pühler (Bio/Technology 9, 84–87 (1991) I.B.R., in Reinscheid et al. (Applied and Environmental Microbiology 60, 126–132 (1994)) I.B.R., in LaBarre et al. (Journal of Bacteriology 175 I.B.R., 1001–1007 (1993)) I.B.R., in WO 96/15246 I.B.R., in Malumbres et al. (Gene 134, 15–24 (1993)) I.B.R., in JP-A-10-229891 I.B.R., in Jensen and Hammer (Biotechnology and Bioengineering 58, 191–195 (1998)) I.B.R., in Makrides (Microbiological Reviews 60:512–538 (1996)) I.B.R. and in known textbooks of genetics and molecular biology.

For the purposes of enhancement, the sigM gene of the invention was overexpressed, for example, with the aid of episomal plasmids. Suitable plasmids are those which are replicated in coryneform bacteria. Many known plasmid vectors, such as, for example, pZ1 (Menkel et al., Applied and Environmental Microbiology (1989) 64: 549–554 I.B.R.), pEKEx1 (Eikmanns et al., Gene 102:93–98 (1991) I.B.R.) or pHS2-1 (Sonnen et al., Gene 107:69–74 (1991) I.B.R.), are based on the cryptic plasmids pHM1519, pBL1 or pGA1. Other plasmid vectors, such as, for example, those which are based on pCG4 (U.S. Pat. No. 4,489,160 I.B.R.) or pNG2 (Serwold-Davis et al., FEMS Microbiology Letters 66, 119–124 (1990) I.B.R.) or pAG1 (U.S. Pat. No. 5,158,891 I.B.R.), may likewise be used.

Also suitable are those plasmid vectors with the aid of which the process of gene amplification can be applied by integration into the chromosome, as has been described, for example, by Reinscheid et al. (Applied and Environmental Microbiology 60, 126–132 (1994)) I.B.R. for the duplication or amplification of the hom-thrB operon. In that method, the complete gene is cloned into a plasmid vector that is able to replicate in a host (typically *E. coli*), but not in *C. glutamicum*. Suitable vectors are, for example, pSUP301 (Simon et al., Bio/Technology 1, 784–791 (1983) I.B.R.), pK18mob or pK19mob (Schäfer et al., Gene 145, 69–73 (1994) I.B.R.), PGEM-T (Promega Corporation, Madison, Wiss., USA), pCR2.1-TOPO (Shuman (1994). Journal of Biological Chemistry 269: 32678–32684 I.B.R.; U.S. Pat. No. 5,487,993 I.B.R.), pCR®Blunt (Invitrogen, Groningen, Netherlands; Bernard et al., Journal of Molecular Biology, 234: 534–541 (1993) I.B.R.), pEM1 (Schrumpf et al., 1991, Journal of Bacteriology 173:4510–4516 I.B.R.) or pBGS8 (Spratt et al., 1986, Gene 41:337–342 I.B.R.). The plasmid vector containing the gene to be amplified is then transferred to the desired strain of *C. glutamicum* by conjugation or transformation. The method of conjugation is described, for example, in Schäfer et al. (Applied and Environmental Microbiology 60, 756–759 (1994)) I.B.R. Methods of transformation are described, for example, in Thierbach et al. (Applied Microbiology and Biotechnology 29, 356–362 (1988)) I.B.R., Dunican and Shivnan (Bio/Technology 7, 1067–1070 (1989)) I.B.R. and Tauch et al. (FEMS Microbiological Letters 123, 343–347 (1994)) I.B.R. After homologous recombination by means of a "cross-over" occurrence, the resulting strain contains at least two copies of the gene in question.

In addition, it may be advantageous for the production of L-amino acids to enhance, especially to overexpress, in addition to the sigM gene, one or more enzymes of the biosynthesis pathway in question, of glycolysis, of the anaplerotic pathway, of the citric acid cycle, of the pentose phosphate cycle, of amino acid export, and, optionally, regulatory proteins.

Accordingly, for the production of L-amino acids, in addition to enhancing the endogenous sigM gene, one or more genes selected from the group the gene dapA coding for dihydrodipicolinate synthase (EP-B 0 197 335 I.B.R.), the gene gap coding for glyceraldehyde-3-phosphate dehydrogenase (Eikmanns (1992), Journal of Bacteriology 174:6076–6086 I.B.R.), the gene tpi coding for triose phosphate isomerase (Eikmanns (1992), Journal of Bacteriology 174:6076–6086 I.B.R.), the gene pgk coding for 3-phosphoglycerate kinase (Eikmanns (1992), Journal of Bacteriology 174:6076–6086 I.B.R.), the gene zwf coding for glucose-6-phosphate dehydrogenase (JP-A-09224661 I.B.R.), the gene pyc coding for pyruvate carboxylase (DE-A-198 31 609 I.B.R.), the gene mqo coding for malate quinone oxidoreductase (Molenaar et al., European Journal of Biochemistry 254, 395–403 (1998) I.B.R.), the gene lysC coding for a feed-back resistant aspartate kinase (Accession No. P26512; EP-B-0387527 I.B.R.; EP-A-0699759 I.B.R.), the gene lysE coding for lysine export (DE-A-195 48 222 I.B.R.), the gene hom coding for homoserine dehydrogenase (EP-A 0131171 I.B.R.), the gene ilvA coding for threonine dehydratase (Möckel et al., Journal of Bacteriology (1992) 8065–8072) I.B.R.) or the allele ilvA(Fbr) coding for a feed-back resistant threonine dehydratase (Möckel et al., (1994) Molecular Microbiology 13: 833–842 I.B.R.), the gene ilvBN coding for acetohydroxy acid synthase (EP-B 0356739 I.B.R.), the gene ilvD coding for dihydroxy acid hydratase (Sahm and Eggeling (1999) Applied and Environmental Microbiology 65: 1973–1979 I.B.R.), the gene zwa1 coding for the Zwa1 protein (DE: 19959328.0 I.B.R., DSM 13115)

may be enhanced, especially overexpressed.

Furthermore, it may be advantageous for the production of L-amino acids, in addition to enhancing the sigM gene, to attenuate, especially to diminish the expression of, one or more genes selected from the group the gene pck coding for phosphoenol pyruvate carboxykinase (DE 199 50 409.1 I.B.R.; DSM 13047), the gene pgi coding for glucose-6-phosphate isomerase (U.S. Ser. No. 09/396,478 I.B.R.; DSM 12969), the gene poxB coding for pyruvate oxidase (DE: 1995 1975.7 I.B.R.; DSM 13114), the gene zwa2 coding for the Zwa2 protein (DE: 19959327.2 I.B.R., DSM 13113).

The term "attenuation" in this context describes the reduction or exclusion of the intracellular activity of one or more enzymes (proteins) in a microorganism that are coded for by the corresponding DNA, by, for example, using a weak promoter or using a gene or allele that codes for a corresponding enzyme having a low level of activity, or by inactivating the corresponding gene or enzyme (protein), and optionally combining those measures.

By the measures of attenuation, the activity or concentration of the corresponding protein is generally lowered to from 0 to 75%, from 0 to 50%, from 0 to 25%, from 0 to 10% or from 0 to 5% of the activity or concentration of the wild-type protein, or of the activity or concentration of the protein in the starting microorganism.

It may also be advantageous for the production of amino acids, in addition to overexpression of the sigM gene, to exclude undesired secondary reactions (Nakayama: "Breeding of Amino Acid Producing Microorganisms", in: Overproduction of Microbial Products, Krumphanzl, Sikyta, Vanek (eds.), Academic Press, London, UK, 1982 I.B.R.).

The microorganisms produced according to the invention also form part of the invention and can be cultivated, for the purposes of the production of amino acids, continuously or discontinuously in the batch, fed batch or repeated fed batch process. A summary of known cultivation methods is described in the textbook of Chmiel (Bioprozeßtechnik 1. Einführung in die Bioverfahrenstechnik (Gustav Fischer Verlag, Stuttgart, 1991)) I.B.R. or in the textbook of Storhas (Bioreaktoren und periphere Einrichtungen (Vieweg Verlag, Braunschweig/Wiesbaden, 1994)) I.B.R.

The culture medium to be used must meet the requirements of the strains in question in a suitable manner. Descriptions of culture media for various microorganisms are to be found in the handbook "Manual of Methods for General Bacteriology" of the American Society for Bacteriology (Washington D.C., USA, 1981) I.B.R.

There may be used as the carbon source sugars and carbohydrates, such as, for example, glucose, saccharose, lactose, fructose, maltose, molasses, starch and cellulose, oils and fats, such as, for example, soybean oil, sunflower oil, groundnut oil and coconut oil, fatty acids, such as, for example, palmitic acid, stearic acid and linoleic acid, alcohols, such as, for example, glycerol and ethanol, and organic acids, such as, for example, acetic acid. Those substances may be used individually or in the form of a mixture.

There may be used as the nitrogen source organic nitrogen-containing compounds, such as peptones, yeast extract, meat extract, malt extract, corn steep liquor, soybean flour and urea, or inorganic compounds, such as ammonium sulfate, ammonium chloride, ammonium phosphate, ammonium carbonate and ammonium nitrate. The nitrogen sources may be used individually or in the form of a mixture.

There may be used as the phosphorus source phosphoric acid, potassium dihydrogen phosphate or dipotassium hydrogen phosphate or the corresponding sodium-containing salts. The culture medium must also contain salts of metals, such as, for example, magnesium sulfate or iron sulfate, which are necessary for growth. Finally, essential growth substances, such as amino acids and vitamins, may be used in addition to the above-mentioned substances. Suitable precursors may also be added to the culture medium. The mentioned substances may be added to the culture in the form of a single batch, or they may be fed in in a suitable manner during the cultivation.

In order to control the pH value of the culture, basic compounds, such as sodium hydroxide, potassium hydroxide, ammonia or ammonia water, or acid compounds, such as phosphoric acid or sulfuric acid, are expediently used. In order to control the development of foam, anti-foams, such as, for example, fatty acid polyglycol esters, may be used. In order to maintain the stability of plasmids, suitable substances having a selective action, such as, for example, antibiotics, may be added to the medium. In order to maintain aerobic conditions, oxygen or gas mixtures containing oxygen, such as, for example, air, are introduced into the culture. The temperature of the culture is normally from 20° C. to 45° C. and preferably from 25° C. to 40° C. The culture is continued until the maximum amount of the desired product has formed. That aim is normally achieved within a period of from 10 hours to 160 hours.

Methods of determining L-amino acids are known from the prior art. The analysis may be carried out, for example, as described in Spackman et al. (Analytical Chemistry, 30, (1958), 1190) I.B.R. by ion-exchange chromatography with subsequent ninhydrin derivation, or it may be carried out by reversed phase HPLC, as described in Lindroth et al. (Analytical Chemistry (1979) 51: 1167–1174) I.B.R.

The process of the invention is used for the production of amino acids by fermentation.

The present invention is explained in greater detail below by means of Examples.

The following microorganism was deposited as a pure culture on 18$^{th}$ Jul. 2001 at the Deutsche Sammlung für Mikroorganismen und Zellkulturen (DSMZ, German Collection of Microorganisms and Cell Cultures, Mascheroder Weg 1b D-38124 Braunschweig, Germany) in accordance with the Budapest treaty:

*Escherichia coli* DH5amcr/pEC-XK99EsigMalex as DSM 14409

The isolation of plasmid DNA from *Escherichia coli* and all techniques for restriction, Klenow and alkaline phosphatase treatment were carried out according to Sambrook et al. (Molecular Cloning. A Laboratory Manual (1989) Cold Spring Harbor Laboratory Press, Cold Spring Harbor, N.Y., USA) I.B.R. Methods for the transformation of *Escherichia coli* are also described in that handbook.

The composition of common nutrient media, such as LB or TY medium, will also be found in the handbook of Sambrook et al.

EXAMPLE 1

Preparation of a Genomic Cosmid Gene Library from *Corynebacterium glutamicum* ATCC 13032

Chromosomal DNA from *Corynebacterium glutamicum* ATCC 13032 was isolated as described in Tauch et al. (1995, Plasmid 33:168–179) I.B.R. and partially cleaved with the restriction enzyme Sau3AI (Amersham Pharmacia, Freiburg, Germany, product description Sau3AI, Code no. 27-0913-02). The DNA fragments were dephosphorylated with shrimp alkaline phosphatase (Roche Diagnostics GmbH, Mannheim, Germany, product description SAP, Code no. 1758250). The DNA of the cosmid vector Super-Cos1 (Wahl et al. (1987) Proceedings of the National Academy of Sciences USA 84:2160–2164 I.B.R.), obtained from Stratagene (La Jolla, USA, product description Super-Cos1 Cosmid Vektor Kit, Code no. 251301), was cleaved with the restriction enzyme XbaI (Amersham Pharmacia, Freiburg, Germany, product description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, product description BamHI, Code no. 27-0868-04). The cosmid DNA so treated was mixed with the treated ATCC13032 DNA, and the batch was treated with T4-DNA ligase (Amersham Pharmacia, Freiburg, Germany, product description T4-DNA ligase, Code no. 27-0870-04). The ligation mixture was then packed in phages with the aid of Gigapack II XL Packing Extract (Stratagene, La Jolla, USA, product description Gigapack II XL Packing Extract, Code no. 200217).

For infection of *E. coli* strain NM554 (Raleigh et al. 1988, Nucleic Acid Research 16:1563–1575 I.B.R.), the cells were taken up in 10 mM $MgSO_4$ and mixed with an aliquot of the phage suspension. Infection and titration of the cosmid library were carried out as described in Sambrook et al. (1989, Molecular Cloning: A Laboratory Manual, Cold Spring Harbor I.B.R.), the cells being plated out on LB agar (Lennox, 1955, Virology, 1:190 I.B.R.) with 100 mg/l ampicillin. After incubation overnight at 37° C., recombinant individual clones were selected.

EXAMPLE 2

Isolation and Sequencing of the SigM Gene

The cosmid DNA of an individual colony was isolated using the Qiaprep Spin Miniprep Kit (Product No. 27106, Qiagen, Hilden, Germany) according to the manufacturer's instructions, and partially cleaved with the restriction enzyme Sau3AI (Amersham Pharmacia, Freiburg, Germany, product description Sau3AI, Product No. 27-0913-02). The DNA fragments were dephosphorylated with shrimp alkaline phosphatase (Roche Diagnostics GmbH, Mannheim, Germany, product description SAP, Product No. 1758250). After separation by gel electrophoresis, cosmid fragments having a size in the range from 1500 to 2000 bp were isolated using the QiaExII Gel Extraction Kit (Product No. 20021, Qiagen, Hilden, Germany).

The DNA of sequencing vector pZero-1, obtained from Invitrogen (Groningen, Netherlands, product description Zero Background Cloning Kit, Product No. K2500-01), was cleaved with the restriction enzyme BamHI (Amersham Pharmacia, Freiburg, Germany, product description BamHI, Product No. 27-0868-04). Ligation of the cosmid fragments into the sequencing vector pZero-1 was carried out as described by Sambrook et al. (1989, Molecular Cloning: A Laboratory Manual, Cold Spring Harbor) I.B.R., the DNA mixture being incubated overnight with T4 ligase (Pharmacia Biotech, Freiburg, Germany). The ligation mixture was

```
sigMex1:
5' ga tctaga tat gta gca cct cag cga ca 3'      SEQ ID NO:3 sigMex2:
5' ct ctgcag ctt cca tca gtt gct ttc gc 3'      SEQ ID NO:4
``` then electroporated into *E. coli* strain DH5αMCR (Grant, 1990, Proceedings of the National Academy of Sciences U.S.A., 87:4645–4649 I.B.R.) (Tauch et al. 1994, FEMS Microbiol Letters, 123:343–347 I.B.R.) and plated out on LB agar (Lennox, 1955, Virology, 1:190 I.B.R.) with 50 mg/l Zeocin.

Plasmid preparation of the recombinant clones was carried out using the Biorobot 9600 (Product No. 900200, Qiagen, Hilden, Germany). Sequencing was effected by the dideoxy chain termination method of Sanger et al. (1977, Proceedings of the National Academy of Sciences U.S.A., 74:5463–5467) I.B.R. with modifications according to Zimmermann et al. (1990, Nucleic Acids Research, 18:1067) I.B.R. The "RR dRhodamin Terminator Cycle Sequencing Kit" from PE Applied Biosystems (Product No. 403044, Weiterstadt, Germany) was used. Separation by gel electrophoresis and analysis of the sequencing reaction was carried out in a "Rotiphorese NF Acrylamid/Bisacrylamid" gel (29:1) (Product No. A124.1, Roth, Karlsruhe, Germany) using the "ABI Prism 377" sequencing device from PE Applied Biosystems (Weiterstadt, Germany).

The resulting crude sequence data were then processed using the Staden program package (1986, Nucleic Acids Research, 14:217–231 I.B.R.) Version 97–0. The individual sequences of the pzero1 derivatives were assembled to a coherent contig. The computer-assisted coding region analysis was prepared using the program XNIP (Staden, 1986, Nucleic Acids Research, 14:217–231 I.B.R.). Further analyses were carried out with the "BLAST search program" (Altschul et al., 1997, Nucleic Acids Research, 25:3389–3402 I.B.R.), against the non-redundant databank of the "National Center for Biotechnology Information" (NCBI, Bethesda, Md., USA).

The relative degree of substitution or mutation in the polynucleotide or amino acid sequence to produce a desired percentage of sequence identity can be established or determined by well-known methods of sequence analysis. These methods are disclosed and demonstrated in Bishop, et al. "DNA & Protein Sequence Analysis (A Practical Approach"), Oxford Univ. Press, Inc. (1997) I.B.R. and by Steinberg, Michael "Protein Structure Prediction" (A Practical Approach), Oxford Univ. Press, Inc. (1997) I.B.R.

The resulting nucleotide sequence is shown in SEQ ID No. 1. Analysis of the nucleotide sequence gave an open reading frame of 675 base pairs, which is designated the sigM gene. The sigM gene codes for a protein of 224 amino acids.

EXAMPLE 3

3.1 Cloning of the SigM Gene

Chromosomal DNA isolated from the strain ATCC 13032 by the method of Eikmanns et al. (Microbiology 140: 1817–1828 (1994)) I.B.R. On the basis of the sequence of the sigM gene known from Example 2 for *C. glutamicum*, the following oligonucleotides were selected for the polymerase chain reaction (see SEQ ID No. 3 and SEQ ID No. 4):

The primers shown were synthesized by MWG-Biotech AG (Ebersberg, Germany) and the PCR reaction was carried out according to the standard PCR method of Innis et al. (PCR Protocols. A Guide to Methods and Applications, 1990, Academic Press) I.B.R. with Pwo polymerase from Roche Diagnostics GmbH (Mannheim, Germany). With the aid of the polymerase chain reaction, the primers permit amplification of a DNA fragment 743 bp in size that carries the sigM gene. In addition, the primer sigMex1 contains the sequence for the cleavage site of the restriction endonuclease XbaI, and the primer sigMex2 contains the cleavage site of the restriction endonuclease PstI, which are indicated in the above nucleotide sequence by underlining.

The sigM fragment 743 bp in size was cleaved with the restriction endonucleases XbaI and PstI and then isolated from the agarose gel using the QiaExII Gel Extraction Kit (Product No. 20021, Qiagen, Hilden, Germany).

3.2 Construction of the Shuttle Vector pEC-XK99E

The *E. coli*-*C. glutamicum* shuttle vector pEC-XK99E was constructed according to the prior art. The vector contains the replication region rep of plasmid pGA1 including the replication effector per (U.S. Pat. No. 5,175,108 I.B.R.; Nesvera et al., Journal of Bacteriology 179, 1525–1532 (1997)) I.B.R., the kanamycin resistance gene aph(3')-IIa from *Escherichia coli* (Beck et al. (1982), Gene 19: 327–336 I.B.R.), the origin of replication, the trc promoter, the termination regions T1 and T2, the lacI$^q$ gene (repressor of the lac operon of *E. coli*) and a multiple cloning site (mcs) (Norrander, J. M. et al. Gene 26, 101–106 (1983) I.B.R.) of plasmid pTRC99A (Amann et al. (1988), Gene 69: 301–315 I.B.R.). The trc promoter can be induced by addition of the lactose derivative IPTG (isopropyl β-D-thiogalactopyranoside).

The constructed *E. coli*-*C. glutamicum* shuttle vector pEC-XK99E was transferred to *C. glutamicum* DSM5715 by means of electroporation (Liebl et al., 1989, FEMS Microbiology Letters, 53:299–303 I.B.R.). Selection of the transformants was carried out on LBHIS agar consisting of 18.5 g/l brain-heart infusion broth, 0.5 M sorbitol, 5 g/l Bacto tryptone, 2.5 g/l Bacto yeast extract, 5 g/l NaCl and 18 g/l Bacto agar, which had been supplemented with 25 mg/l kanamycin. Incubation was carried out for 2 days at 33° C.

Plasmid DNA was isolated from a transformant by the conventional methods (Peters-Wendisch et al., 1998, Microbiology, 144, 915–927 I.B.R.), cleaved with the restriction endonuclease HindIII, and the plasmid was examined by subsequent agarose gel electrophoresis.

The plasmid construct so obtained was designated pEC-XK99E (FIG. 1). The strain obtained by electroporation of plasmid pEC-XK99E into C. glutamicum strain DSM5715 was named DSM5715/pEC-XK99E and deposited as DSM13455 at the Deutsche Sammlung für Mikroorganismen und Zellkulturen (DSMZ, Braunschweig, Germany) in accordance with the Budapest treaty.

3.3 Cloning of SigM into the E. Coli-C. Glutamicum Shuttle Vector pEC-XK99E

The E. coli-C. glutamicum shuttle vector pEC-XK99E described in Example 3.2 was used as the vector. DNA of that plasmid was cleaved completely with the restriction enzymes XbaI and PstI and then dephosphorylated with shrimp alkaline phosphatase (Roche Diagnostics GmbH, Mannheim, Germany, product description SAP, Product No. 1758250).

The sigM fragment approximately 741 bp in size, described in Example 3.1, obtained by means of PCR and cleaved with the restriction endonucleases XbaI and PstI, was mixed with the prepared vector pEC-XK99E and the batch was treated with T4-DNA ligase (Amersham Pharmacia, Freiburg, Germany, product description T4-DNA ligase, Code no. 27–0870–04). The ligation batch was transformed into E. coli strain DH5αmcr (Hanahan, in: DNA cloning. A Practical Approach. Vol. I. IRL-Press, Oxford, Washington D.C., USA) I.B.R. The selection of plasmid-carrying cells was effected by plating out the transformation batch on LB agar (Lennox, 1955, Virology, 1:190 I.B.R.) with 50 mg/l kanamycin. After incubation overnight at 37° C., recombinant individual clones were selected. Plasmid DNA was isolated from a transformant using the Qiaprep Spin Miniprep Kit (Product No. 27106, Qiagen, Hilden, Germany) according to the manufacturer's instructions and was cleaved with the restriction enzymes XbaI and PstI in order to examine the plasmid by subsequent agarose gel electrophoresis. The resulting plasmid was named pEC-XK99EsigMa1ex. It is shown in FIG. 2.

EXAMPLE 4

Transformation of Strain DSM5715 with the Plasmid pEC-XK99EsigMa1ex

Strain DSM5715 was transformed with the plasmid pEC-XK99EsigMa1ex using the electroporation method described by Liebl et al., (FEMS Microbiology Letters, 53:299–303 (1989)) I.B.R. Selection of the transformants was carried out on LBHIS agar consisting of 18.5 g/l brain-heart infusion broth, 0.5 M sorbitol, 5 g/l Bacto tryptone, 2.5 g/l Bacto yeast extract, 5 g/l NaCl and 18 g/l Bacto agar, which had been supplemented with 25 mg/l kanamycin. Incubation was carried out for 2 days at 33° C.

Plasmid DNA was isolated from a transformant by the conventional methods (Peters-Wendisch et al., 1998, Microbiology, 144, 915–927 I.B.R.), cleaved with the restriction endonucleases XbaI and PstI, and the plasmid was examined by subsequent agarose gel electrophoresis. The resulting strain was named DSM5715/pEC-XK99EsigMa1ex.

EXAMPLE 5

Production of Lysine

The C. glutamicum strain DSM5715/pEC-XK99EsigMa1ex obtained in Example 4 was cultivated in a nutrient medium suitable for the production of lysine, and the lysine content in the culture supernatant was determined.

To that end, the strain was first incubated for 24 hours at 33° C. on agar plate with the corresponding antibiotic (brain-heart agar with kanamycin (25 mg/l). Starting from that agar plate culture, a pre-culture was inoculated (10 ml of medium in a 100 ml Erlenmeyer flask). CgIII complete medium was used as the medium for the pre-culture.

|  | Cg III medium |
| --- | --- |
| NaCl | 2.5 g/l |
| Bacto peptone | 10 g/l |
| Bacto yeast extract | 10 g/l |
| Glucose (autoclaved separately) | 2% (w/v) |

The pH value was adjusted to pH 7.4

Kanamycin (25 mg/l) was added thereto. The pre-culture was incubated for 16 hours at 33° C. at 240 rpm on a shaker. A main culture was inoculated from that pre-culture, so that the initial OD (660 nm) of the main culture was 0.1. MM medium was used for the main culture.

|  | MM medium |
| --- | --- |
| CSL (corn steep liquor) | 5 g/l |
| MOPS (morpholinopropane sulfonic acid) | 20 g/l |
| Glucose (autoclaved separately) | 50 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterilized by filtration) | 0.3 mg/l |
| Thiamin * HCl (sterilized by filtration) | 0.2 mg/l |
| L-Leucine (sterilized by filtration) | 0.1 g/l |
| $CaCO_3$ | 25 g/l |

CSL, MOPS and the salt solution were adjusted to pH 7 with ammonia water and autoclaved. The sterile substrate and vitamin solutions were then added, as well as the dry autoclaved $CaCO_3$.

Cultivation was carried out in a volume of 10 ml in a 100 ml Erlenmeyer flask with baffles. Kanamycin (25 mg/l) and IPTG (1 mM/l) were added. Cultivation was carried out at 33° C. and 80% humidity.

After 72 hours, the OD was determined at a measuring wavelength of 660 nm using a Biomek 1000 (Beckmann Instruments GmbH, Munich). The amount of lysine that had formed was determined using an amino acid analyzer from Eppendorf-BioTronik (Hamburg, Germany) by ion-exchange chromatography and post-column derivation with ninhydrin detection.

The result of the test is shown in Table 1.

TABLE 1

| Strain | OD (660 nm) | Lysine HCl g/l |
| --- | --- | --- |
| DSM5715 | 11.8 | 14.43 |
| DSM5715/pEC-XK99EsigMalex | 9.0 | 14.82 |

This application claims priority to German Priority Document Application No. 100 43 337.5, filed on Sep. 2, 2000 and to German Priority Document Application No. 101 36 984.0, filed on Jul. 28, 2001. Both German Priority Documents are hereby incorporated by reference in their entirety.

We claim:

1. An isolated polynucleotide sequence which encodes a polypeptide comprising the amino acid sequence of SEQ ID No. 2.

2. An isolated polynucleotide comprising nucleotides 236 to 907 of SEQ ID NO: 1.

3. An isolated polynucleotide comprising the nucleotide sequence of SEQ ID No. 1.

4. An isolated polynucleotide comprising the nucleotide sequence of the complete complement of nucleotides 236 to 907 of SEQ ID NO: 1.

5. An isolated polynucleotide comprising the nucleotide sequence of the complete complement of SEQ ID NO: 1.

6. A vector comprising the polynucleotide of any one of claims 3, 1, 2, 4 or 5.

7. The vector according to claim 6, wherein said vector is pEC-XK99sigMa1ex as deposited in DSM14409.

8. A bacterium comprising the polynucleotide of any one of claims 3, 1, 2, 4 or 5, wherein said bacterium is an *E. coli* or a coryneform bacterium.

9. A bacterium comprising the vector of claim 6, wherein said bacterium is an *E. coli* or a coryneform bacterium.

10. An *Escherichia coli* strain DH5amcr/pEC-XK99EsigMa1ex deposited as DSM 14409.

11. A recombinant *Corynebacterium glutamicum* comprising an overexpressed polynucleotide encoding a polypeptide having the amino acid sequence of SEQ ID NO:2, wherein overexpression is achieved by increasing the copy number of said polynucleotide or by operably linking a promoter to said polynucleotide.

12. A method for the production of L-amino acids using coryneform bacteria comprising:
   fermenting coryneform bacteria comprising an overexpressed sigM polynucleotide wherein said polynucleotide comprises a nucleotide sequence according to any one of claims 3, 1, or 2,
wherein said overexpression is achieved by increasing the copy number of said polynucleotide or by operably linking said polynucleotide to a promoter.

13. The method according to claim 12, further comprising:
   b) isolating the L-amino acids.

14. The method as claimed in claim 12, wherein the L-amino acid produced is L-lysine.

15. The method according to claim 12, wherein the bacteria are *Corynebacterium glutamicum*.

16. The method as claimed in claim 12, wherein the bacteria comprise, at the same time, one or more *Corynebacterium glutamicum* genes which are overexpressed, wherein the one or more genes is/are selected from the group consisting of:
   the dapA gene coding for dihydrodipicolinate synthase,
   the gap gene coding for glyceraldehyde-3-phosphate dehydrogenase,
   the tpi gene coding for triose phosphate isomerase,
   the pgk gene coding for 3-phosphoglycerate kinase,
   the zwf gene coding for glucose-6-phosphate dehydrogenase,
   the pyc gene coding for pyruvate carboxylase,
   the mqo gene coding for malate quinone oxidoreductase,
   the lysC gene coding for feed-back resistant aspartate kinase,
   the lysE gene coding for lysine export protein,
   the hom gene coding for homoserine dehydrogenase,
   the ilvA gene coding for threonine dehydratase or the ilvA(Fbr) allele coding for feed-back resistant threonine dehydratase,
   the ilvBN gene coding for acetohydroxy acid synthase,
   the ilvD gene coding for dihydroxy acid hydratase, and
   the zwa1 gene coding for the Zwa1 protein.

17. The method as claimed in claim 12, wherein the bacteria are *Corynebacterium glutamicum* and comprise, at the same time, one or more endogenous *Corynebacterium glutamicum* genes which are eliminated, wherein the one or more genes is/are selected from the group consisting of:
   the pck gene coding for phosphoenol pyruvate,
   the pgi gene coding for glucose-6-phosphate isomerase,
   the poxB gene coding for pyruvate oxidase, and
   the zwa2 gene coding for the Zwa2 protein.

* * * * *

SEQUENCE LISTING

<160> NUMBER OF SEQ ID NOS: 4

<210> SEQ ID NO 1
<211> LENGTH: 1211
<212> TYPE: DNA
<213> ORGANISM: Corynebacterium glutamicum
<220> FEATURE:
<221> NAME/KEY: CDS
<222> LOCATION: (236)..(907)
<223> OTHER INFORMATION:

<400> SEQUENCE: 1

```
gacaccaatc cacagatgca gatcgctgaa gtacaacttg ttggttggta aattacgcgt      60
ttgtgattga cccccattaa ggtgcgcccg ccctcagttt cactaactga aggcgggcgt     120
ttttaattta tatatagctt cagctcacag gtattttcca gaaagaagag ccctcaaagt     180
atgtagcacc tcagcgacac ctcccacttg agtgggcgcc gagaagtatc tctca atg     238
                                                              Met
                                                               1 gaa aat ctg ccc ata cta agc cgc ata agg gat acg ggg tgt gtc cct      286
Glu Asn Leu Pro Ile Leu Ser Arg Ile Arg Asp Thr Gly Cys Val Pro
        5                  10                  15 caa cct gcg ggg gat ctt atg aca gta ctg cct aaa aac cat gac cta      334
Gln Pro Ala Gly Asp Leu Met Thr Val Leu Pro Lys Asn His Asp Leu
     20                  25                  30 agc gat acc caa ctc gtc aaa cag ttt ata tct ggc gac tcc agg gca      382
Ser Asp Thr Gln Leu Val Lys Gln Phe Ile Ser Gly Asp Ser Arg Ala
 35                  40                  45 ttt tcc acc atc att cac cgc cac gaa cga cat atg atg cag gca gcc      430
Phe Ser Thr Ile Ile His Arg His Glu Arg His Met Met Gln Ala Ala
 50                  55                  60                  65 aga aaa tac ggg cgg aaa cca gaa gac gcc caa gac att ctc caa gaa      478
Arg Lys Tyr Gly Arg Lys Pro Glu Asp Ala Gln Asp Ile Leu Gln Glu
             70                  75                  80 gct ctc ttt cgc gcc agc cga aac atg cac ctt tat aga gca gaa gca      526
Ala Leu Phe Arg Ala Ser Arg Asn Met His Leu Tyr Arg Ala Glu Ala
         85                  90                  95 gct ctc ggc acg tgg ctc cac aaa ctt gtc ctg aat agc ggc ttc gat      574
Ala Leu Gly Thr Trp Leu His Lys Leu Val Leu Asn Ser Gly Phe Asp
        100                 105                 110 tgg gct acc cac cgc tcc caa gta gaa ttc ccc atc ctt aac gaa cca      622
Trp Ala Thr His Arg Ser Gln Val Glu Phe Pro Ile Leu Asn Glu Pro
    115                 120                 125 aca atc gat tta gaa aaa gat cct cgc cta gcc acc gac ccc ttg ggc      670
Thr Ile Asp Leu Glu Lys Asp Pro Arg Leu Ala Thr Asp Pro Leu Gly
130                 135                 140                 145 tac ctc gat gtc gcc atg aca att cga tcc gcc atc gac caa tta cac      718
Tyr Leu Asp Val Ala Met Thr Ile Arg Ser Ala Ile Asp Gln Leu His
                150                 155                 160 ccc gat caa cgc atc gcc tta ata ctt gtc gac ctc ggc ggc tac acc      766
Pro Asp Gln Arg Ile Ala Leu Ile Leu Val Asp Leu Gly Gly Tyr Thr
            165                 170                 175 gta gaa gat gtg gcc gaa atc gaa gga atc aaa gta ggt acc gtt aaa      814
Val Glu Asp Val Ala Glu Ile Glu Gly Ile Lys Val Gly Thr Val Lys
        180                 185                 190 tca cgc cga ggg cgc gca cgc aaa gcg ttg cgc gcc ctt tta cat gca      862
Ser Arg Arg Gly Arg Ala Arg Lys Ala Leu Arg Ala Leu Leu His Ala
    195                 200                 205
```

```
gat ttc ttc ggg ccc gaa gat ggc tcc ata cag tgc gaa agc aac       907
Asp Phe Phe Gly Pro Glu Asp Gly Ser Ile Gln Cys Glu Ser Asn
210                 215                 220 tgatggaagt ttttcaaagt gtctgacgtt gaaaacggtg agttcacaac tagggtgaat   967
ggtgcacgtg atgctgcact tttacgttta ctactttgag ggaaacaatg tctgaagaac  1027
aatctgccgt agcaccaaag attcatgatg tcgccatcat cggctccggt ccagctggct  1087
ataccgcagc agtatatgca gcccgcgctg acctcaaccc catcatgttc gagggctatg  1147
aatacggtgg atctttgatg accactactg acgtggaaaa cttcccaggc tttgaaaagg  1207
gaat                                                              1211
```

<210> SEQ ID NO 2
<211> LENGTH: 224
<212> TYPE: PRT
<213> ORGANISM: Corynebacterium glutamicum

<400> SEQUENCE: 2

```
Met Glu Asn Leu Pro Ile Leu Ser Arg Ile Arg Asp Thr Gly Cys Val
1               5                   10                  15

Pro Gln Pro Ala Gly Asp Leu Met Thr Val Leu Pro Lys Asn His Asp
            20                  25                  30

Leu Ser Asp Thr Gln Leu Val Lys Gln Phe Ile Ser Gly Asp Ser Arg
        35                  40                  45

Ala Phe Ser Thr Ile Ile His Arg His Glu Arg His Met Met Gln Ala
    50                  55                  60

Ala Arg Lys Tyr Gly Arg Lys Pro Glu Asp Ala Gln Asp Ile Leu Gln
65                  70                  75                  80

Glu Ala Leu Phe Arg Ala Ser Arg Asn Met His Leu Tyr Arg Ala Glu
                85                  90                  95

Ala Ala Leu Gly Thr Trp Leu His Lys Leu Val Leu Asn Ser Gly Phe
            100                 105                 110

Asp Trp Ala Thr His Arg Ser Gln Val Glu Phe Pro Ile Leu Asn Glu
        115                 120                 125

Pro Thr Ile Asp Leu Glu Lys Asp Pro Arg Leu Ala Thr Asp Pro Leu
    130                 135                 140

Gly Tyr Leu Asp Val Ala Met Thr Ile Arg Ser Ala Ile Asp Gln Leu
145                 150                 155                 160

His Pro Asp Gln Arg Ile Ala Leu Ile Leu Val Asp Leu Gly Gly Tyr
                165                 170                 175

Thr Val Glu Asp Val Ala Glu Ile Glu Gly Ile Lys Val Gly Thr Val
            180                 185                 190

Lys Ser Arg Arg Gly Arg Ala Arg Lys Ala Leu Arg Ala Leu Leu His
        195                 200                 205

Ala Asp Phe Phe Gly Pro Glu Asp Gly Ser Ile Gln Cys Glu Ser Asn
    210                 215                 220
```

<210> SEQ ID NO 3
<211> LENGTH: 28
<212> TYPE: DNA
<213> ORGANISM: Corynebacterium glutamicum

<400> SEQUENCE: 3
caggtacctg gctacgagga cgattaag                                      28

<210> SEQ ID NO 4

-continued

```
<211> LENGTH: 28
<212> TYPE: DNA
<213> ORGANISM: Corynebacterium glutamicum

<400> SEQUENCE: 4
tgtctagaaa gcatgcggag gaatcaac                                            28
```